US008182664B2

(12) United States Patent
Hiraiwa et al.

(10) Patent No.: US 8,182,664 B2
(45) Date of Patent: May 22, 2012

(54) SENSOR CONTROL DEVICE

(75) Inventors: Masamichi Hiraiwa, Aichi (JP);
Nobuhiro Inoue, Gifu (JP); Satoshi Teramoto, Aichi (JP); Yukinobu Nagao, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 691 days.

(21) Appl. No.: 12/115,840

(22) Filed: May 6, 2008

(65) Prior Publication Data
US 2008/0277281 A1      Nov. 13, 2008

(30) Foreign Application Priority Data
May 7, 2007    (JP) .............................. P2007-122543

(51) Int. Cl.
*G01N 27/419*    (2006.01)
(52) U.S. Cl. ........ 204/424; 204/425; 204/426; 204/428; 204/427; 205/783.5; 205/781; 205/785; 73/23.31; 73/23.32
(58) Field of Classification Search .......... 204/424–429; 205/783.5–785, 781; 73/23.31–23.32
See application file for complete search history.

(56) References Cited

U.S. PATENT DOCUMENTS

| 5,172,677 | A |   | 12/1992 | Suzuki |   |
|---|---|---|---|---|---|
| 5,340,462 | A | * | 8/1994 | Suzuki | 204/425 |
| 5,518,600 | A | * | 5/1996 | Uchinami | 204/401 |
| 5,895,564 | A | * | 4/1999 | Miyata et al. | 205/784.5 |
| 5,976,350 | A |   | 11/1999 | Yamada et al. |   |
| 6,453,720 | B1 |   | 9/2002 | Tomisawa |   |
| 7,713,391 | B2 |   | 5/2010 | Inoue et al. |   |
| 2002/0162743 | A1 | * | 11/2002 | Inagaki | 204/425 |
| 2004/0084309 | A1 | * | 5/2004 | Ando et al. | 204/426 |
| 2006/0157348 | A1 |   | 7/2006 | Inoue et al. |   |

FOREIGN PATENT DOCUMENTS

| JP | 61-294355 A | 12/1986 |
|---|---|---|
| JP | 4-204370 A | 7/1992 |
| JP | 8-075700 A | 3/1996 |
| JP | 2006-208363 A | 8/2006 |

OTHER PUBLICATIONS

Japanese Office Action issued Feb. 21, 2012; in corresponding Office Action No. 2008-111906.

* cited by examiner

*Primary Examiner* — Keith Hendricks
*Assistant Examiner* — Bach Dinh
(74) *Attorney, Agent, or Firm* — Sughrue Mion, PLLC (57) ABSTRACT

A sensor control device for controlling a current application state of a gas sensor element when measuring a specific gas component concentration in a gas to be measured using the gas sensor element, which sensor control device includes: at least one cell having a solid electrolyte body and a pair of electrodes; a sensor heating unit as defined herein; an oxygen reference pole generating unit as defined herein; a damage avoidance time elapse determining unit as defined herein; and a reference generation current application permitting unit as defined herein.

5 Claims, 6 Drawing Sheets

SENSOR CONTROL DEVICE

BACKGROUND OF THE INVENTION

1. Field of the Invention

The present invention relates to a sensor control device that controls a current application state of a gas sensor element, which has at least one cell having a solid electrolyte body and a pair of electrodes, when measuring a specific gas component concentration in a gas to be measured using the gas sensor element.

2. Description of the Related Art

In the related art, a sensor control device is known that controls a current application state of a gas sensor element, which has at least one cell having a solid electrolyte body and a pair of electrodes, when measuring a specific gas component concentration in a gas to be measured using the gas sensor element.

An example of the gas sensor element is a wideband air-fuel ratio sensor provided with an oxygen pump cell and an oxygen concentration detection cell, and an example of the sensor control device is a gas sensor control device that controls the wideband air-fuel ratio sensor (see, for example JP-A-10-73564 corresponding to U.S. Pat. No. 5,976,350, FIG. 1, etc.).

Such a gas sensor control device controls a current application state of the gas sensor element so that the specific gas component concentration can be measured by heating the gas sensor element to an activation temperature using a sensor heating unit (for example, a heater) and passing a reference generation current through the oxygen concentration detection cell to thereby cause one of the pair of electrodes to function as an oxygen reference pole.

3. Problems to be Solved by the Invention

However, in the case where heating of the gas sensor element (solid electrolyte body) performed by the sensor heating unit is not sufficient (in the case where the gas sensor element is not activated), the gas sensor element may be damaged since an overvoltage may be applied to the oxygen concentration detection cell when causing a reference generation current to flow.

That is, in the case where activation of the gas sensor element is not sufficient, reaching a specified current flow through the oxygen concentration detection cell is difficult because an element impedance value of the oxygen concentration detection cell is high. Accordingly, if a preset reference generation current is caused to flow, a large voltage must be applied across the oxygen concentration detection cell. As a result, an overvoltage is applied to the oxygen concentration detection cell, and damage (for example, blackening) of the gas sensor element may occur if the overvoltage is applied for a long period of time.

SUMMARY OF THE INVENTION

The present invention has been made in view of the above-noted problems, and an object thereof is to provide a sensor control device capable of preventing a gas sensor element from being damaged upon application of a reference generation current after start of heating of the gas sensor element.

The above object has been achieved, according to a first aspect of the invention, by providing a sensor control device for controlling a current application state of a gas sensor element when measuring a specific gas component concentration in a gas to be measured using the gas sensor element, the sensor control device comprising: at least one cell comprising a solid electrolyte body and a pair of electrodes a sensor heating unit that heats the gas sensor element; an oxygen reference pole generating unit that causes a reference generation current to flow through at least one cell so as to establish one of the pair of electrodes of the cell as an oxygen reference pole; a damage avoidance time elapse determining unit that determines whether or not a preset damage avoidance time has elapsed from the start of heating of the gas sensor element by the sensor heating unit; and a reference generation current application permitting unit that does not permit the reference generation current to flow when the damage avoidance time elapse determining unit determines that the damage avoidance time has not elapsed, and permits the reference generation current to flow when the damage avoidance time elapse determining unit determines that the damage avoidance time has elapsed.

Since the sensor control device includes the damage avoidance time elapse determining unit and the reference generation current application permitting unit, the sensor control device is configured so as not to permit the reference generation current to flow when the damage avoidance time elapse determining unit determines that the damage avoidance time has not elapsed, from the start of heating of the gas sensor element by the sensor heating unit.

Accordingly, the flow of reference generation current by the oxygen reference pole generating unit is prevented under a situation where the temperature of the gas sensor element is low, such as a situation immediately after the start of heating of the gas sensor element by the sensor heating unit. As a result, it is possible to prevent the gas sensor element from being damaged (for example, blackening) due to application of the reference generation current before the sensor element has been activated.

In addition, the sensor control device is configured to permit of the flow of the reference generation current by the oxygen reference pole generating unit when it is determined that the damage avoidance time has elapsed from the start of heating of the gas sensor element by the sensor heating unit. That is, at the start of reference generation current flow by the oxygen reference pole generating unit, the gas sensor element has been heated during the damage avoidance time by the sensor heating unit. Accordingly, the gas sensor element is in an activated state to some extent.

In this manner, since the flow of the reference generation current can be started by the oxygen reference pole generating unit in a state where the gas sensor element is activated to some extent, an overvoltage applied to the gas sensor element (specifically, the cell) can be prevented. As a result, it is possible to prevent the gas sensor element from becoming damaged due to application of the reference generation current.

Consequently, according to the sensor control device of the present invention, damage (for example, blackening) of the gas sensor element due to application of the reference generation current after the start of heating of the gas sensor element but prior to activation can be prevented. In addition, according to the sensor control device of the present invention, damage to the gas sensor element can be prevented due to application of the reference generation current even if an overvoltage application preventing circuit (limiter circuit) for preventing an overvoltage from being applied between a pair of electrodes of the cell to which the reference generation current is applied is not provided.

In addition, with regard to setting the damage avoidance time, the correlation between the heating time and the element temperature of the gas sensor element may be measured using an actual gas sensor element, and then a suitable value may be set beforehand as the damage avoidance time on the basis of the measurement result. For example, the time required to raise the element temperature of the gas sensor element to a temperature at which damage (for example, blackening) caused by application of the reference generation current does not occur, by heating of the sensor element by the sensor heating unit, may be calculated based on the measurement result, and the calculation result may be set beforehand as the damage avoidance time.

Furthermore, according to a second aspect of the invention, the sensor control device described above may further include: an element temperature detecting unit that detects a temperature of the gas sensor element; and a permission temperature determining unit that compares a current application permission temperature, which is set based on an activation temperature of the gas sensor element, with the element temperature detected by the element temperature detecting unit and determines whether or not the element temperature is higher than the current application permission temperature. The reference generation current application permitting unit may be configured to permit the reference generation current to flow when the damage avoidance time elapse determining unit determines that the damage avoidance time has elapsed or when the permission temperature determining unit determines that the element temperature is higher than the current application permission temperature.

The sensor control device is configured to further include the element temperature detecting unit and the permission temperature determining unit, and to permit the reference generation current to flow when the permission temperature determining unit determines that the element temperature is higher than the current application permission temperature. That is, the sensor control device permits the reference generation current to flow either when the damage avoidance time has elapsed, or when the element temperature is higher than the current application permission temperature.

Thus, application of the reference generation current can be started without waiting for the damage avoidance time to elapse in the case when the element temperature of the gas sensor element reaches the current application permission temperature before the damage avoidance time has elapsed.

In addition, in the case where the element temperature of the gas sensor element is higher than room temperature (for example, 25° C.) at the start of heating by the sensor heating unit, the element temperature may reach the current application permission temperature before the damage avoidance time has elapsed. Thus, in the case when heating by the sensor heating unit is started in a state where the temperature of the gas sensor element is already high, the reference generation current may be allowed to flow through the gas sensor element at an early stage based on the state of the element temperature.

In addition, with regard to setting the current application permission temperature, the reference generation current may be caused to flow using an actual gas sensor element so as to measure the correlation between the element temperature and a damage occurrence situation of the gas sensor element, and then a suitable value may be set beforehand as the current application permission temperature based on the measurement result. For example, it may be possible to specify, on the basis of the measurement result, a temperature range where damage in the gas sensor element occurs and a temperature range where damage does not occur when the reference generation current is caused to flow and to set a value, which is equal to or larger than the boundary temperature between the temperature ranges, as the current application permission temperature beforehand.

Furthermore, according to a third aspect of the present invention, the sensor control device described above may further include: a current application unit that causes a current to flow through the cell, through which the reference generation current is passed, during a preset voltage detection time which is shorter than the damage avoidance time and for which damage caused by current application does not occur; a voltage detecting unit that detects a value of a voltage developed across the pair of electrodes of the cell when a current is caused to flow through the cell by the current application unit; and a permission voltage determining unit that compares a voltage value detected by the voltage detecting unit with a current application permission threshold value, and determines whether or not the voltage value is higher than the current application permission threshold value. The reference generation current application permitting unit may be configured to permit the reference generation current to flow when the damage avoidance time elapse determining unit determines that the damage avoidance time has elapsed or when the permission voltage determining unit determines that the voltage value is lower than the current application permission threshold value.

The sensor control device is configured to further include the current application unit, the voltage detecting unit, and the permission voltage determining unit and to permit the reference generation current to flow when the permission voltage determining unit determines that the voltage value is lower than the current application permission threshold value. That is, the sensor control device permits the reference generation to flow either when the damage avoidance time has elapsed, or when a value of a voltage developed across a pair of electrodes of the cell is lower than the current application permission threshold value.

Thus, application of the reference generation current can be started without waiting for the damage avoidance time to elapse in the case when the value of the voltage developed across the pair of electrodes of the cell becomes lower than the current application permission threshold value before the damage avoidance time has elapsed.

In addition, in the case where the element temperature of the gas sensor element is relatively high at the start of sensor heating, the value of the voltage developed across the pair of electrodes of the cell may be lower than the current application permission threshold value before the damage avoidance time has elapsed. Thus, in the case when heating by the sensor heating unit is started in a state where the temperature of the gas sensor element is already high, the reference generation current may be allowed to flow through the gas sensor element in an early stage based on the state of the element temperature.

Therefore, according to the sensor control device according to the second aspect and/or the third aspect described above, it becomes possible to permit the reference generation current to flow without waiting for the damage avoidance time to elapse under the condition in which the gas sensor element can be activated early. As a result, measurement of the specific gas component concentration can be executed at an early stage.

In addition, an example of the condition in which the temperature of the gas sensor element at the start of sensor heating by the sensor heating unit is higher than room temperature or the condition in which a voltage developed across a pair of electrodes of a cell at the start of sensor heating by the sensor heating unit is relatively low includes a case where the sensor control device is rebooted within a short period of time after stopping the sensor control device.

In addition, with regard to setting the current application permission temperature, the reference generation current may be caused to flow using an actual gas sensor element so as to measure the correlation between the element temperature and a damage occurrence situation of the gas sensor element, and then a suitable value may be set beforehand as the current application permission temperature based on the measurement result. For example, it may be possible to specify, on the basis of the measurement result, a temperature range where damage in the gas sensor element occurs and a temperature range where damage does not occur when the reference generation current is caused to flow and to set a value, which is equal to or larger than the boundary temperature between the temperature ranges, as the current application permission temperature beforehand.

Also, with regard to setting the current application permission temperature, the reference generation current may be caused to flow using an actual gas sensor element so as to measure the correlation between a value of the voltage developed across the pair of electrodes of the cell and the damage occurrence situation of the gas sensor element, and then a suitable value may be set beforehand as the current application permission temperature based on the measurement result.

Furthermore, according to a fourth aspect of the present invention, in the sensor control device of the second aspect of the invention, the sensor control device further comprises a current application unit that causes a current to flow through the cell, through which the reference generation current is passed, during a preset voltage detection time which is shorter than the damage avoidance time and for which damage caused by current application does not occur; a voltage detecting unit that detects a value of the voltage developed across the pair of electrodes of the cell when a current is caused to flow through the cell by the current application unit; and a permission voltage determining unit that compares a voltage value detected by the voltage detecting unit with a current application permission threshold value, and determines whether or not the voltage value is higher than the current application permission threshold value, wherein the reference generation current application permitting unit permits the reference generation current to flow when the damage avoidance time has elapsed or when the permission voltage determining unit determines that the damage avoidance time has elapsed or when the permission voltage determined unit determines that the voltage value is lower than the current application permission threshold value.

In the fourth aspect of the invention, the voltage detecting unit detects a value of a voltage developed across the pair of electrodes of the cell when a current is caused to flow through the cell by the current application unit.

In causing a current flow through the cell during the voltage detection time, a current application unit may be provided separately from the oxygen reference pole generating unit. In this case, however, the circuit size becomes large, which may increase the cost of the sensor control device. In contrast, it becomes possible to cause a current to flow through the cell during the voltage detection time without additionally providing a current application unit by using the oxygen reference pole generating unit also as the current application unit.

Next, for the gas sensor element controlled by the above-described sensor control device, various configurations may be adopted as long as the gas sensor element is configured to include at least one cell. For example, according to a fifth aspect of the present invention, the gas sensor element may include: a measurement chamber communicating with the gas to be measured through a diffusion resistance portion; an oxygen concentration detection cell in which one of a pair of electrodes is blocked so as not to be exposed to the gas to be measured and the other electrode is disposed facing the measurement chamber and which generates a voltage between the pair of electrodes corresponding to an oxygen concentration of the measurement chamber; and an oxygen pump cell in which one of a pair of electrodes is disposed facing the measurement chamber and the other electrode is disposed facing the gas to be measured and which pumps oxygen into or out of the measurement chamber according to a current flowing between the pair of electrodes. The oxygen reference pole generating unit may be connected to the oxygen concentration detection cell such that the one of a pair of electrodes of the oxygen concentration detection cell becomes an oxygen reference pole.

In the case of controlling the gas sensor element with such a configuration, the oxygen reference pole generating unit causes the reference generation current to flow through the oxygen concentration detection cell in order to make one (the electrode that is blocked so as not to be exposed to the gas to be measured) of the pair of electrodes of the oxygen concentration detection cell function as an oxygen reference pole.

In addition, the gas sensor element provided with the oxygen concentration detection cell and the oxygen pump cell may be used for detecting oxygen or NOx in the exhaust gas of an internal combustion engine. In such application, the start time of application of the reference generation current may be set to an early time after start of the internal combustion engine such that early gas detection becomes possible. Accordingly, the reference generation current may be applied under the situation where the gas sensor element is not activated. As a result, the gas sensor element may be damaged.

In contrast, since the sensor control device of the present invention initiates flow of the reference generation current by the oxygen reference pole generating unit in a state where the gas sensor element is sufficiently activated as described above, application of an overvoltage to the gas sensor element (specifically, the oxygen concentration detection cell) can be prevented. As a result, it is possible to prevent the gas sensor element from being damaged due to application of the reference generation current.

Consequently, even in the case of a gas sensor element in which early application of the reference generation current is requested, it is possible to prevent the gas sensor element from becoming damaged due to application of the reference generation current by using the sensor control device of the present invention.

DESCRIPTION OF REFERENCE NUMERALS

Reference numerals used to identify various structural features in the drawings include the following.
1: internal combustion engine control system
2: gas sensor driving circuit
5: electronic control unit
8: gas sensor
9: engine control device
10: gas sensor element
14: oxygen pump cell
18: porous diffusion layer
20: measurement chamber
24: oxygen concentration detection cell
26: reference oxygen chamber
43: heater
60: heater control circuit

DETAILED DESCRIPTION OF THE INVENTION

Hereinafter, preferred embodiments of the present invention will be described with reference to the accompanying drawings. However, the present invention should not be construed as being limited thereto.

Figure 1:
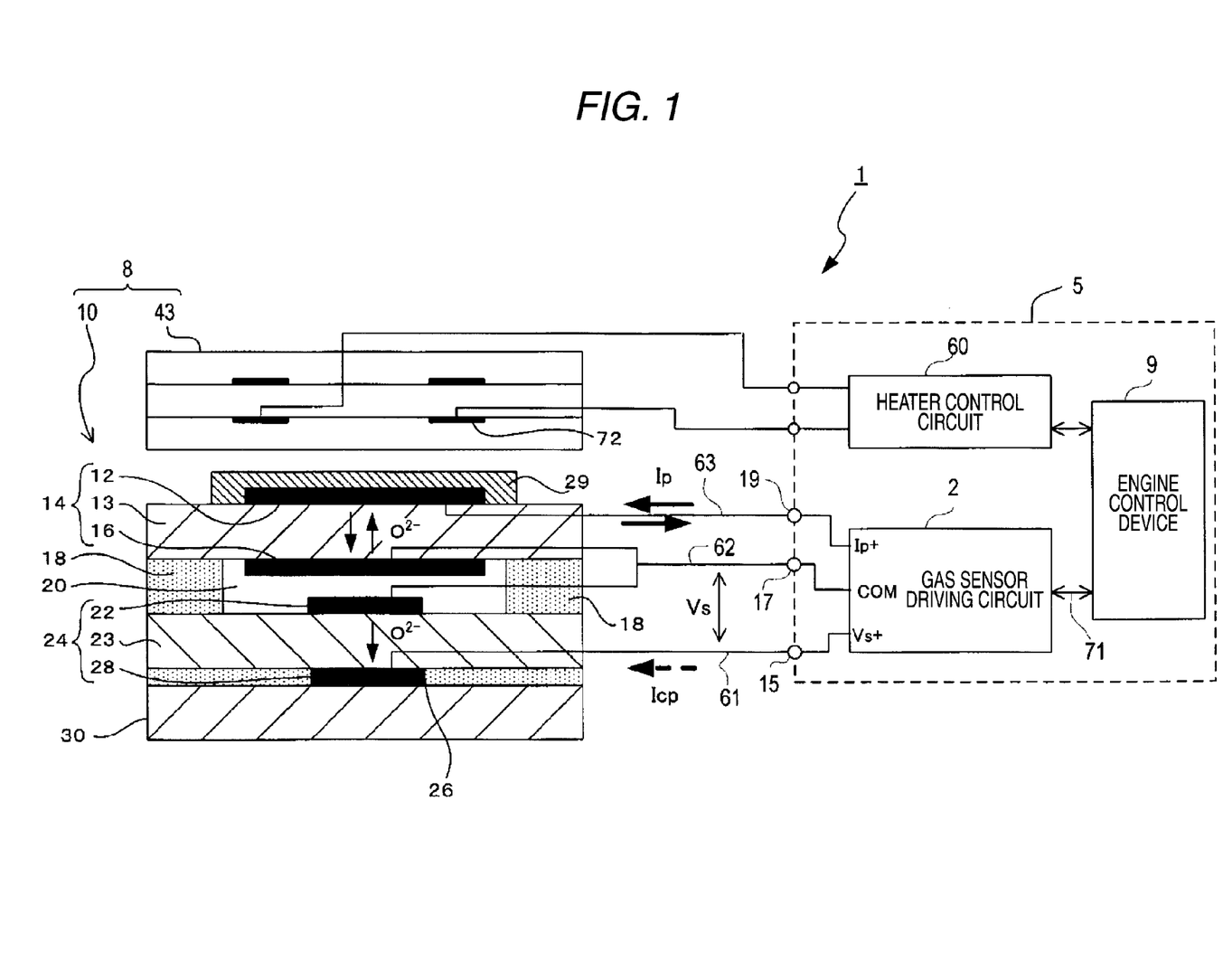
FIG. 1 is a view illustrating a schematic configuration of an internal combustion engine control system including an electronic control unit to which the present invention is applied.

First, a view illustrating the schematic configuration of an internal combustion engine control system 1 including an electronic control unit 5 to which the present invention is applied is shown in FIG. 1.

The internal combustion engine control system 1 executes various kinds of control processing for controlling an operation state of an internal combustion engine (hereinafter, also referred to as an engine). As an example, the internal combustion engine control system 1 executes processing for detecting the concentration of a specific gas (for example, oxygen) contained in exhaust gas. In addition, the internal combustion engine control system 1 performs processing (air-fuel ratio detection processing) for detecting the air-fuel ratio of an internal combustion engine based on the detected gas component concentration and performs processing (air-fuel ratio control processing) for controlling an operation state (for example, throttle opening or the amount of fuel supply) of the internal combustion engine so that the air-fuel ratio of the internal combustion engine reaches a target air-fuel ratio.

The internal combustion engine control system 1 is configured to include the electronic control unit 5 and a gas sensor 8. In addition, the electronic control unit 5 is configured to include a gas sensor driving circuit 2, an engine control device 9 and a heater control circuit 60.

The gas sensor 8 is configured to include a gas sensor element 10 which detects the oxygen concentration in exhaust gas over a wide range (in other words, in which an output signal is approximately proportional to the oxygen concentration in the exhaust gas) and a heater 43 for maintaining the gas sensor element 10 at the operating temperature.

The gas sensor element 10 detects the oxygen concentration in the exhaust gas over a wide range and is configured to include an oxygen pump cell 14, a porous diffusion layer 18, an oxygen concentration detection cell 24 and a reinforcing plate 30.

The oxygen pump cell 14 has an oxygen ion conductive solid electrolyte body 13, which is formed in a plate shape from partially stabilized zirconia ($ZrO_2$), and a first pump electrode 12 and a second pump electrode 16 that are mainly formed of platinum on front and bottom surfaces of the solid electrolyte body 13, respectively. The first pump electrode 12 is electrically connected to a third connection terminal 19 of the electronic control unit 5 through a wiring line 63, and the second pump electrode 16 is electrically connected to a second connection terminal 17 of the electronic control unit 5 through a wiring line 62. In addition, the first pump electrode 12 is covered with a porous protective layer 29, thereby being protected from a poisoning material and the like by the porous protective layer 29.

In addition, the oxygen concentration detection cell 24 has an oxygen ion conductive solid electrolyte body 23, which is formed in a plate shape from partially stabilized zirconia ($ZrO_2$), and a first detection electrode 22 and a second detection electrode 28 that are mainly formed of platinum on front and bottom surfaces of the solid electrolyte body 23, respectively. The first detection electrode 22 is electrically connected to the second connection terminal 17 of the electronic control unit 5 through the wiring line 62 and is also electrically connected to the second pump electrode 16. The second detection electrode 28 is electrically connected to the first connection terminal 15 of the electronic control unit 5 through a wiring line 61.

An insulating layer (not shown) that is mainly formed of an insulating material (for example, alumina) is interposed between the oxygen pump cell 14 and the oxygen concentration detection cell 24 in order to electrically insulate cells 14 and 24 from one another, and the porous diffusion layer 18 is provided in a part of the insulating layer. In addition, the porous diffusion layer 18 is included as a porous portion (diffusion resistance portion) that is mainly formed of an insulating material (for example, alumina) in a porous shape. The porous diffusion layer 18 provides for diffusion rate control of the gas to be measured that is introduced inside the gas sensor element 10.

A hollow measuring chamber 20 surrounded by the porous diffusion layer 18 and the insulating layer (not shown) is formed between the oxygen pump cell 14 and the oxygen concentration detection cell 24. That is, the measuring chamber 20 communicates with a measurement gas atmosphere (measured gas space) through the porous diffusion layer 18 (more specifically, a porous portion). In addition, the second pump electrode 16 and the first detection electrode 22 are disposed in the measuring chamber 20.

Moreover, although the diffusion rate control portion is formed using a porous diffusion layer 18 in the present embodiment, a small opening may also be provided as a diffusion rate control side portion instead of the porous diffusion layer 18 in order to control the speed of introduction of gas, which is to be measured, into the measuring chamber 20.

The reinforcing plate 30 is disposed to adhere to a surface of the oxygen concentration detection cell 24 not facing the measuring chamber 20 with the second detection electrode 28 interposed therebetween. Thus, the reinforcing plate 30 serves to improve the overall strength of the gas sensor element 10.

In addition, the second detection electrode 28 of the oxygen concentration detection cell 24 is in a blocked state with respect to the gas to be measured due to the reinforcing plate 30, and a reference oxygen chamber 26 as a sealed space is formed in the inside and periphery of the second detection electrode 28 between the oxygen concentration detection cell 24 and the reinforcing plate 30.

In the gas sensor element 10 having such a configuration, oxygen with an approximately fixed concentration is accumulated in the reference oxygen chamber 26 formed in the inside and periphery of the second detection electrode 28. This is achieved by causing a low constant current Icp (hereinafter, referred to as a reference generation current Icp), which is a fixed current value, to flow in the direction from the second detection electrode 28 of the oxygen concentration detection cell 24 to the first detection electrode 22 and pumping oxygen from the measuring chamber 20 to a side of the second detection electrode 28. Thus, oxygen with the approximately fixed concentration accumulated in the reference oxygen chamber 26 serves as a reference oxygen concentration when detecting the oxygen concentration of measured gas in the gas sensor element 10. For this reason, the second detection electrode 28 is also called a self-generation reference electrode.

In addition, the oxygen concentration detection cell 24 generates a voltage corresponding to the oxygen concentration difference between a pair of electrodes (between the first detection electrode 22 and the second detection electrode 28). In addition, since the oxygen concentration of the reference oxygen chamber 26 that the second detection electrode 28 faces is set to the approximately fixed concentration and the second detection electrode 28 functions as the self-generation reference electrode as described above, the oxygen concentration detection cell 24 is configured to generate a voltage (electromotive force) corresponding to the oxygen concentration of the measuring chamber 20 across a pair of electrodes.

In addition, the oxygen pump cell 14 is configured to control pumping of oxygen out of the measuring chamber 20 or pumping of oxygen into the measuring chamber 20 according to the current flow direction of a current flowing between the pair of electrodes (the first pump electrode 12 and the second pump electrode 16). In addition, the oxygen pump cell 14 is configured to adjust the amount of pumped oxygen according to the magnitude of the current flowing between the pair of electrodes.

The reinforcing plate 30 has approximately the same size as the solid electrolyte bodies 13 and 23 that form the oxygen pump cell 14 and the oxygen concentration detection cell 24, respectively, and is formed in a plate shape using a material with ceramic as a main constituent.

The heater 43 is formed in the shape of a flat plate and is disposed to face the oxygen pump cell 14 of the gas sensor element 10. The heater 43 is formed using a material with alumina as a main constituent and has a heater wiring line 72, which is formed using a material with platinum as a main constituent, thereinside. The heater 43 is controlled such that the temperature of the gas sensor element 10 reaches the activation temperature (for example, 550 to 900° C.) by power supplied from the heater control circuit 60 to be described below. In addition, both ends of the heater wiring line 72 are electrically connected to the heater control circuit 60.

In addition, the gas sensor 8 changes to a state where gas detection (oxygen detection) is possible when the gas sensor element 10 (more specifically, the oxygen pump cell 14 and the oxygen concentration detection cell 24) is activated by heating of the heater 43.

Next, as described above, the electronic control unit 5 is configured to include the gas sensor driving circuit 2 which controls the gas sensor element 10, the heater control circuit 60 which controls the heater 43, and the engine control device 9 which controls the gas sensor driving circuit 2 and the heater control circuit 60.

First, the gas sensor driving circuit 2 includes a Vs+ terminal, a COM terminal, and an Ip+ terminal. These terminals are electrically connected to the first connection terminal 15, the second connection terminal 17, and the third connection terminal 19 of the electronic control unit 5, respectively. Accordingly, the second detection electrode 28 of the gas sensor element 10 is electrically connected to the Vs+ terminal of the gas sensor driving circuit 2 through the first connection terminal 15. In addition, the first detection electrode 22 and the second pump electrode 16 of the gas sensor element 10 are electrically connected to the COM terminal of the gas sensor driving circuit 2 through the second connection terminal 17. In addition, the first pump electrode 12 of the gas sensor element 10 is electrically connected to the Ip+ terminal of the gas sensor driving circuit 2 through the third connection terminal 19.

In addition, the gas sensor driving circuit 2 detects a gas detection signal and an element impedance signal from the gas sensor 8 provided in the exhaust pipe of the internal combustion engine (engine), and outputs the gas detection signal and the element impedance signal to the engine control device 9 (hereinafter, referred to as an engine CPU 9). In addition, the gas detection signal changes with the oxygen concentration in the exhaust gas, the element impedance signal changes with the electrical resistance value of the gas sensor 8, and the electrical impedance value changes with the temperature of the gas sensor 8.

Here, among the configurations of the gas sensor driving circuit 2, the configuration for outputting the gas detection signal corresponding to the oxygen concentration will be briefly described.

First, the gas sensor driving circuit 2 controls pumping of oxygen into the measuring chamber 20 and pumping of oxygen out of the measuring chamber 20 by means of the oxygen pump cell 14. More particularly, the gas sensor driving circuit 2 controls a pump current Ip flowing through the oxygen pump cell 14 such that a voltage Vs developed across both ends of the oxygen concentration detection cell 24 is set to 450 mV while causing the reference generation current Icp flow through the oxygen concentration detection cell 24.

In addition, in the gas sensor element 10, oxygen contained in gas to be measured is diffused to the measuring chamber 20 through the porous diffusion layer 18. The gas sensor element 10 generates an electromotive force of 450 mV in the oxygen concentration detection cell 24 due to the oxygen concentration difference between the measuring chamber 20 and the reference oxygen chamber 26, which serves as a reference of the oxygen concentration, when the specific gas component concentration (oxygen concentration) in the gas to be measured is a preset control target value (for example, the oxygen concentration when the air-fuel mixture supplied to the engine is maintained at the theoretical air-fuel ratio).

That is, when the specific gas component concentration (oxygen concentration) in the gas to be measured is different from the control target value, the gas sensor driving circuit 2 performs processing so that the oxygen concentration of the measuring chamber 20 approaches the control target value. Particularly, this is achieved by causing the pump current Ip flow through the oxygen pump cell 14, to thereby pump oxygen into or out of the measuring chamber 20. Accordingly, since the current value and current direction of the pump current Ip flowing through the oxygen pump cell 14 changes with the oxygen concentration in the exhaust gas, the pump current Ip can be used to calculate the oxygen concentration in the exhaust gas.

The gas sensor driving circuit 2 configured in this manner can detect the pump current Ip, which changes with the oxygen concentration in the exhaust gas, and output the gas detection signal, which changes with the current value and current direction of the pump current Ip, to an external device (the engine control device 9 in the present embodiment).

Next, among the configurations of the gas sensor driving circuit 2, the configuration regarding measurement of impedance (temperature) of the gas sensor element 10 (more specifically, the impedance of the oxygen concentration detection cell 24) will be described. In addition, since the measurement of impedance of the gas sensor element 10 (oxygen concentration detection cell 24) is performed by the known circuit configurations represented in JP-A-2006-343317 and JP-A-2002-257783, the configuration regarding the measurement of impedance will be briefly described below.

The gas sensor driving circuit 2 includes a constant current output unit that outputs a current Irpvs for impedance measurement for measuring the impedance of the oxygen concentration detection cell 24, a sample hold circuit that holds the voltage Vs generated across both ends of the oxygen concentration detection cell 24, and a control circuit that executes an ON/OFF control of current flowing to the oxygen concentration detection cell 24 by means of a constant current output unit and control of holding and release of the voltage Vs by the sample hold circuit at different predetermined periods. In addition, the gas sensor driving circuit 2 is configured such that the voltage Vs of the oxygen concentration detection cell 24 can be held in the sample hold circuit immediately before the current Irpvs for resistance measurement is caused to flow through the oxygen concentration detection cell 24.

In addition, the gas sensor driving circuit 2 includes a difference voltage output circuit that compares a hold value (voltage Vs of the oxygen concentration detection cell 24 immediately before the current Irpvs for impedance measurement is caused to flow) held in the sample hold circuit with a voltage Vsh across both ends of the oxygen concentration detection cell 24 when the current Irpvs for impedance measurement is caused to flow through the oxygen concentration detection cell 24 and outputs a difference voltage value ΔVs which is a difference between both voltages. In addition, since the difference voltage value ΔVs is proportional to a bulk impedance value of the oxygen concentration detection cell 24, the difference voltage value ΔVs can be used as an element impedance signal Vrpvs indicating the impedance of the gas sensor element 10 (oxygen concentration detection cell 24).

The gas sensor driving circuit 2 is configured such that the element impedance signal Vrpvs proportional to the bulk impedance value of the oxygen concentration detection cell 24 is output to the engine control device 9. In addition, the element impedance signal Vrpvs is proportional to the bulk impedance value of the oxygen concentration detection cell 24 and changes with the temperature of the oxygen concentration detection cell 24.

Next, the heater control circuit 60 controls the amount of power supplied to the heater 43 and hence the heating amount according to a heater energization command signal from the engine control device 9. For example, when the heater control circuit 60 is configured to output a voltage signal with a pulse waveform to the heater 43, the heater control circuit 60 can control (PWM control, or pulse-width-modulation control) the amount of power supplied to the heater 43 by changing the duty ratio of the pulse waveform according to the heater energization command signal.

Next, the engine control device 9 can be formed using a microcomputer including a CPU serving as a central processing unit, a storage unit (RAM and ROM) which stores data, a program, and the like, and input and output ports through which input and output of signals between the engine control device 9 and an external device are performed.

Furthermore, in the engine control device 9, controls of e.g. the amount of fuel injection is executed based on calculation processed on the basis of the gas detection signal.

The engine control device 9 having such a configuration executes various kinds of control processing, such as specific gas component concentration detection processing for detecting the specific gas component concentration in the exhaust gas on the basis of a gas detection signal from the gas sensor driving circuit 2 and/or air-fuel ratio control processing for controlling the air-fuel ratio of the engine using the gas detection signal. For example, the engine control device 9 performs processing (specific gas component concentration detection processing) for calculating an oxygen concentration value corresponding to the gas detection signal using a map or computation expression stored in a storage unit (for example, a memory) of the engine control device 9 after converting the gas detection signal received from the gas sensor driving circuit 2 into a digital value using an A/D conversion circuit (not shown).

Next, after-start state determination processing executed in the engine control device 9 of the electronic control unit 5 will be described.

The after-start state determination processing is processing executed immediately after starting the electronic control unit 5, where processing (for determining the application start time of the reference generation current Icp and for determining whether or not the gas sensor element 10 is in a state in which a specific gas (oxygen) can be detected) is performed after heating of the gas sensor element 10 is started using the heater 43.

Figure 2:
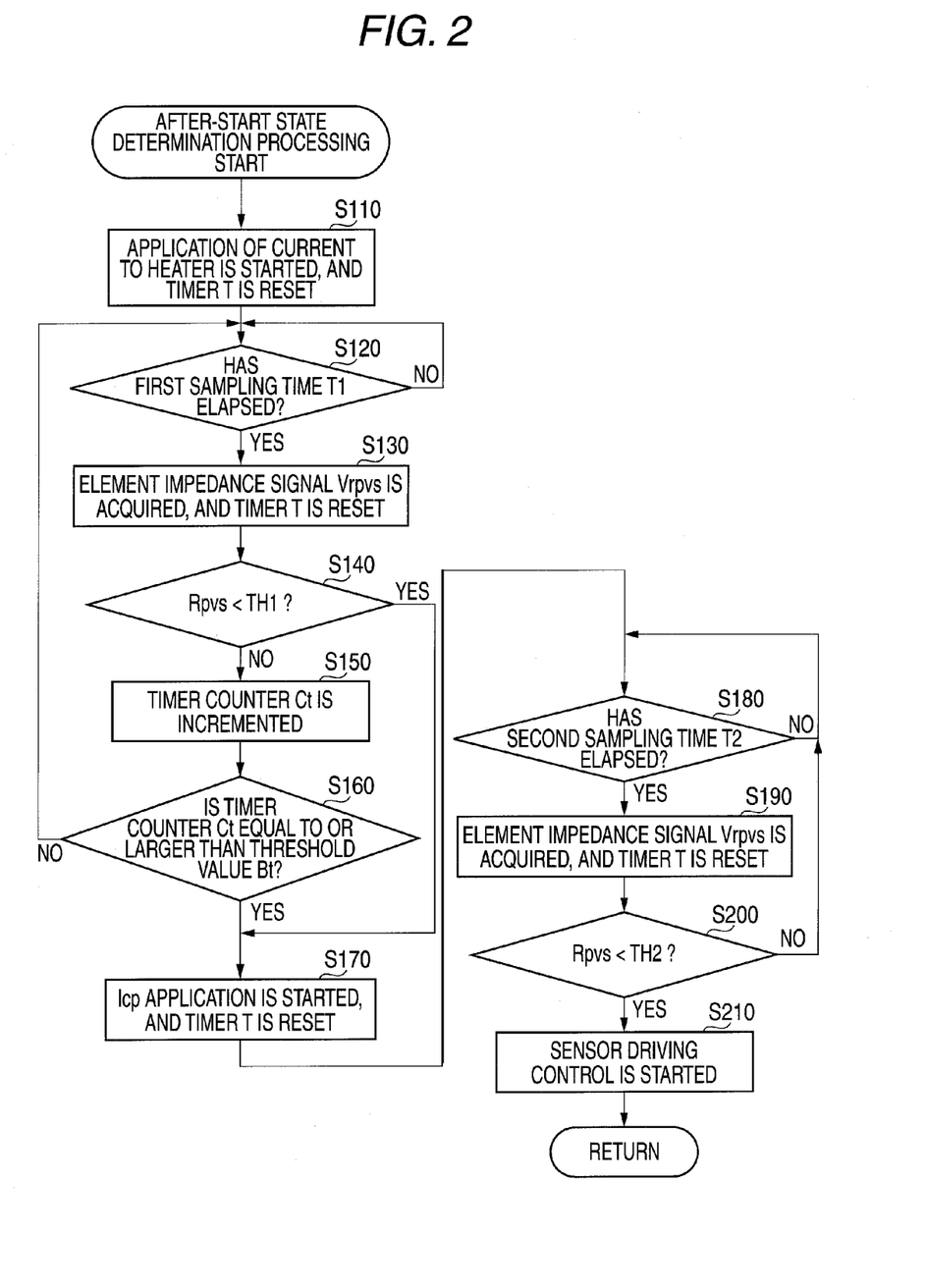
FIG. 2 is a flow chart illustrating processing details of after-start state determination processing in an embodiment of the invention.

FIG. 2 is a flow chart illustrating processing details of the after-start state determination processing.

When the internal combustion engine control system 1 starts, the after-start state determination processing in the engine control device 9 of the electronic control unit 5 is started.

Then, when the after-start state determination processing is started, processing for current application to the heater 43 is first started in step S110 (S indicates step). Specifically, the engine control device 9 outputs a heater energization command signal to the heater control circuit 60. Then, the heater control circuit 60 begins applying current to the heater 43 to heat the gas sensor element 10 and controls a state of current application to the heater 43 such that the gas sensor element 10 reaches a target temperature (activation temperature).

Furthermore, in step S110, after outputting the heater energization command signal, a timer T is reset to start the elapsed time measurement processing using the timer T and processing for initializing (setting to 0) a timer counter Ct used in internal processing is executed.

In the following step S120, in order to determine the sampling time (detection time) of the element impedance signal Vrpvs, a determination is made as to whether or not a first sampling time T1 has elapsed on the basis of the value of the timer T. If a positive determination is made, the process proceeds to step S120. If a negative determination is made, the same step is repeatedly executed and waits until the first sampling time T1 has elapsed.

In addition, in step S120, a determination is made as to whether or not the first sampling time T1 has elapsed on the basis of the value of the timer T when the measurement is started in step S110 or S130 described below. In addition, regarding the first sampling time T1, the detection period (sampling period) of the element impedance signal Vrpvs is preset. The element impedance signal Vrpvs detected at this time is used to determine the application start time of the reference generation current Icp.

When a positive determination is made in step S120 to proceed to step S130, processing for acquiring the element impedance signal Vrpvs is executed in step S130. Specifically, the engine control device 9 is connected to the gas sensor driving circuit 2 through a transmission cable 71 and acquires the element impedance signal Vrpvs from the gas sensor driving circuit 2 through the transmission cable 71.

In addition, as described above, the gas sensor driving circuit 2 repeatedly executes processing for detecting the element impedance signal Vrpvs from the gas sensor 8 (gas sensor element 10), which is provided in the exhaust pipe of the internal combustion engine (engine), by causing the current Irpvs for impedance measurement to flow through the oxygen concentration detection cell 24 of the gas sensor element 10 at a predetermined period and then holding the element impedance signal Vrpvs in the sample hold circuit.

In addition, in step S130, processing for calculating an electrical impedance value Rpvs of the gas sensor 8 (specifically, the oxygen concentration detection cell 24) on the basis of the element impedance signal Vrpvs is executed. In addition, the electrical impedance value Rpvs changes with temperature of the gas sensor 8 (gas sensor element 10). Therefore, the electrical impedance value Rpvs can be used as a variable indicating the element temperature of the gas sensor 8 (gas sensor element 10).

In addition, in step S130, the electrical impedance value Rpvs is calculated and the timer T is reset to start the elapsed time measurement processing using the timer T again.

In the following step S140, a determination is made as to whether or not the electrical impedance value Rpvs is smaller than a first temperature determination value TH1. If a positive determination is made, the process proceeds to step S170. If a negative determination is made, the process proceeds to step S150.

In addition, as the first temperature determination value TH1, an electrical impedance value of the gas sensor element 10 when the temperature of the gas sensor element 10 is a blackening avoidance temperature (temperature at which blackening due to application of the reference generation current Icp does not occur in the gas sensor element 10) is set.

That is, in step S140, a determination is made as to whether or not the element temperature of the gas sensor element 10 exceeds the blackening avoidance temperature. If a positive determination is made, the process proceeds to step S170. If a negative determination is made, the process proceeds to step S150.

When a negative determination is made in step S140 to proceed to step S150, processing for incrementing (adding 1 to) the timer counter Ct is executed. Accordingly, the number of times in which the negative determination has been made in step S140 is recorded as a value of the timer counter Ct, and the timer counter Ct can be used to determine the elapsed time with the heater energization start time (S110) as a base point.

In the following step S160, a determination is made as to whether or not the timer counter Ct is equal to or larger than a damage avoidance determination threshold value Bt. If a positive determination is made, the process proceeds to step S170. If a negative determination is made, the process proceeds to step S120.

In addition, the damage avoidance determination threshold value Bt is preset on the basis of the time (shortest damage avoidance time) required to raise the element temperature of the gas sensor element 10 to a temperature at which damage (for example, blackening) caused by application of the reference generation current does not occur, by heating according to a predetermined current application pattern using the heater 43. Specifically, a value (integer) larger than an operation result when dividing the shortest damage avoidance time by a renewal period (increment period) of the timer counter Ct is set as the damage avoidance determination threshold value Bt. In addition, in the present embodiment, the timer counter Ct and the damage avoidance determination threshold value Bt are all integers.

In addition, by heating the sensor using an actual gas sensor element and measuring the time required until the element temperature of the gas sensor element reaches the temperature at which the reference generation current Icp can flow, the shortest damage avoidance time can be set on the basis of a result of the measurement.

When a positive determination is made in step S140 or a positive determination is made in step S160, the process proceeds to S170. In step S170, processing for application of the reference generation current Icp is started.

Specifically, the gas sensor driving circuit 2 causes the reference generation current Icp to start flowing through the gas sensor element 10 (specifically, the oxygen concentration detection cell 24) by causing the engine control device 9 to output an Icp current application command signal to the gas sensor driving circuit 2.

Thus, oxygen is pumped from the measuring chamber 20 to a side of the second detection electrode 28 by causing the reference generation current Icp to flow as described above. As a result, oxygen with an approximately fixed concentration is finally accumulated in the reference oxygen chamber 26 formed in the inside and periphery of the second detection electrode 28 of the oxygen concentration detection cell 24.

In addition, in step S170, the Icp current application command signal is output to the gas sensor driving circuit 2, and the timer T is reset to start the elapsed time measurement processing using the timer T again.

In the following step S180, a determination is made as to whether or not a second sampling time T2 set beforehand has elapsed with the application start time of the reference generation current Icp as a base point. If a positive determination is made, the process proceeds to step S190. If a negative determination is made, the same step is repeatedly executed and waits until the second sampling time T2 has elapsed.

In addition, in step S180, a determination is made as to whether or not the second sampling time T2 has elapsed on the basis of the value of the timer T when the measurement is started in step S170 or S190 described below. In addition, regarding the second sampling time T2, the detection period (sampling period) of the element impedance signal Vrpvs is set beforehand. The element impedance signal Vrpvs detected at this time is used to determine the start time (in other words, application start time of the pump current Ip) of sensor driving control.

When a positive determination is made in step S180 to proceed to step S190, processing for acquiring the element impedance signal Vrpvs is executed in step S190. In addition, the engine control device 9 acquires the element impedance signal Vrpvs from the gas sensor driving circuit 2 through the transmission cable 71.

In addition, in step S190, processing for calculating the electrical impedance value Rpvs of the gas sensor 8 (specifically, the oxygen concentration detection cell 24) on the basis of the element impedance signal Vrpvs is executed. In addition, the electrical impedance value Rpvs changes with the temperature of the gas sensor 8 (gas sensor element 10).

Therefore, the electrical impedance value Rpvs can be used as a variable indicating the element temperature of the gas sensor 8 (gas sensor element 10).

In addition, in step S190, the electrical impedance value Rpvs is calculated and the timer is reset to start the elapsed time measurement processing using the timer T again.

In the following step S200, a determination is made as to whether or not the electrical resistance value Rpvs is smaller than a second temperature determination value TH2. If a positive determination is made, the process proceeds to step S210. If a negative determination is made, the process proceeds to step S180.

In addition, the second temperature determination value TH2 is set beforehand to be an electrical impedance value of the gas sensor 8 when the temperature of the gas sensor element 10 is at an activation temperature. In addition, a value smaller than the first temperature determination value TH1 is set as the second temperature determination value TH2 (TH2<TH1), and the temperature of the gas sensor element 10 corresponding to the second temperature determination value TH2 is set to a temperature higher than the temperature of the gas sensor element 10 corresponding to the first temperature determination value TH1.

When a positive determination is made in step S200 to proceed to step S210, sensor driving control processing is started in step S210.

Specifically, the gas sensor driving circuit 2 causes the pump current Icp to start flowing through the gas sensor element 10 (specifically, the oxygen pump cell 14) by causing the engine control device 9 to output a sensor driving command signal to the gas sensor driving circuit 2. Then, the gas sensor driving circuit 2 controls the pump current Ip flowing to the oxygen pump cell 14 such that an output voltage of the oxygen concentration detection cell 24 approaches a control target value and outputs a gas detection signal, which changes with current value and current direction of the pump current Ip, to the engine control device 9.

In addition, the engine control device 9 performs processing (specific gas component concentration detection processing) for calculating an oxygen concentration value corresponding to the gas detection signal using a map or computation expression stored in a storage unit (for example, a memory) of the engine control device 9 after converting the gas detection signal received from the gas sensor driving circuit 2 into a digital value using an A/D conversion circuit (not shown).

By executing the after-start state determination processing as described above, the engine control device 9 of the electronic control unit 5 can determine the start time of application of the reference generation current Icp to the gas sensor 8 (gas sensor element 10) or determine whether or not the gas sensor element 10 can detect a specific gas (oxygen).

Thereafter, the engine control device 9 executes various control processing (air-fuel ratio detection processing, air-fuel ratio control processing, and the like) while executing processing for detecting the concentration of a specific gas (for example, oxygen) contained in the exhaust gas by executing the sensor driving control processing.

In this manner, the internal combustion engine control system 1 executes various control processing for controlling the operational state of the internal combustion engine (engine).

Furthermore, in the present embodiment, the electronic control unit 5 corresponds to the sensor control device of the invention, the gas sensor element 10 corresponds to the gas sensor element, the engine control device 9, the heater control circuit 60 and the heater 43 that execute step S110 correspond to the sensor heating unit, and the gas sensor driving circuit 2 corresponds to the oxygen reference pole generating unit.

In addition, the engine control device 9 that executes steps S150 and S160 corresponds to a damage avoidance time elapse determining unit, the engine control device 9 that executes step S170 corresponds to a reference generation current application permitting unit, the gas sensor driving circuit 2 and the engine control device 9 that execute step S130 correspond to an element temperature detecting unit, and the engine control device 9 that executes step S140 corresponds to a permission temperature determining unit.

As described above, in the internal combustion engine control system 1 according to the present embodiment, the electronic control unit 5 is configured to cause the reference generation current Icp to start flowing through the gas sensor element 10 when a predetermined condition is satisfied after starting the apparatus.

That is, the engine control device 9 of the electronic control unit 5 starts application of the reference generation current Icp with the gas sensor driving circuit 2 by executing the after-start state determination processing when a time (damage avoidance time) set by the damage avoidance determination threshold value Bt has elapsed from the heating start time (S110) of the gas sensor element 10 (when the positive determination is made in step S160) (S170).

For this reason, when the gas sensor driving circuit 2 starts applying the reference generation current Icp, the gas sensor element 10 is heated during the damage avoidance time by the heater 43 and the heater control circuit 60. Accordingly, the gas sensor element 10 is in an activated state to at least some extent.

In this manner, since application of the reference generation current Icp can be started by the gas sensor driving circuit 2 in a state where the gas sensor element 10 is activated to some extent, application of an overvoltage to the gas sensor element 10 (specifically, the oxygen concentration detection cell 24) can be prevented. As a result, it is possible to prevent the gas sensor element 10 from becoming damaged due to application of the reference generation current Icp.

In addition, the engine control device 9 of the electronic control unit 5 does not permit application of the reference generation current Icp if the damage avoidance determination threshold value Bt has not elapsed from the heating start time (S110) of the gas sensor element 10 at the time of execution of step S160.

Accordingly, application of the reference generation current Icp to the gas sensor driving circuit 2 can be prevented under a situation where the temperature of the gas sensor element 10 is low, such as a situation immediately after start of sensor heating using the heater 43 and the heater control circuit 60. As a result, it is possible to prevent the gas sensor element 10 from becoming damaged (for example, blackening) due to application of the reference generation current Icp.

Consequently, according to the electronic control unit 5 of the present embodiment, damage (for example, blackening) of the gas sensor element 10 can be prevented due to application of the reference generation current Icp after the start of heating of the gas sensor element 10.

Furthermore, the engine control device 9 of the electronic control unit 5 starts application of the reference generation current Icp with the gas sensor driving circuit 2 by executing the after-start state determination processing even when the element temperature of the gas sensor element 10 exceeds an element temperature (current application permission temperature) set by the first temperature determination value TH1 (when the positive determination is made in step S140) (S170).

That is, the electronic control unit 5 starts application of the reference generation current Icp with the gas sensor driving circuit 2 not only in the case when the damage avoidance time has elapsed from the heating start time (S110) of the gas sensor element 10 (the case when the positive determination is made in step S160), but also in the case when the element temperature of the gas sensor element 10 is determined to be higher than the current application permission temperature (the case when a positive determination is made in step S140) (S170).

Thus, application of the reference generation current Icp can be started by the gas sensor driving circuit 2 without waiting for the damage avoidance time to elapse in the case when the element temperature of the gas sensor element 10 reaches the current application permission temperature before the damage avoidance time has elapsed.

In addition, in the case where the element temperature of the gas sensor element 10 is higher than the room temperature (for example, 25° C.) at the start of sensor heating using the heater 43 and the heater control circuit 60, the element temperature of the gas sensor element 10 may reach the current application permission temperature before the damage avoidance time has elapsed. Thus, in the case when heating using the sensor heating unit is started in a state where the temperature of the gas sensor element 10 already is high, it becomes possible to cause the reference generation current to flow through the gas sensor element 10 at an early stage. This is done by determining whether or not the reference generation current can be applied based on the state of the element temperature, such as by the electronic control unit 5 of the present embodiment.

Therefore, according to the present embodiment, it becomes possible to permit application of the reference generation current Icp without waiting for the damage avoidance time to elapse under the condition in which the gas sensor element 10 can be activated early. As a result, measurement of the specific gas component concentration (oxygen concentration in the present embodiment) can be executed early.

In addition, for example, in the case when the electronic control unit 5 is rebooted within a short period of time after stopping the electronic control unit 5 (internal combustion engine control system 1), the temperature of the gas sensor element 10 does not suddenly drop to room temperature. Rather, the gas sensor element 10 remains in a high temperature state for a period of time. At the time of reboot under such a condition, the element temperature of the gas sensor element 10 may reach the current application permission temperature without waiting for the damage avoidance time to elapse. This is because the element temperature of the gas sensor element 10 at the start of sensor heating is higher than room temperature.

In such a case, it becomes possible to permit application of the reference generation current Icp using the gas sensor element 5 according to the present embodiment, without waiting for the damage avoidance time to elapse. As a result, measurement of the specific gas component concentration can be executed early.

Figure 3:
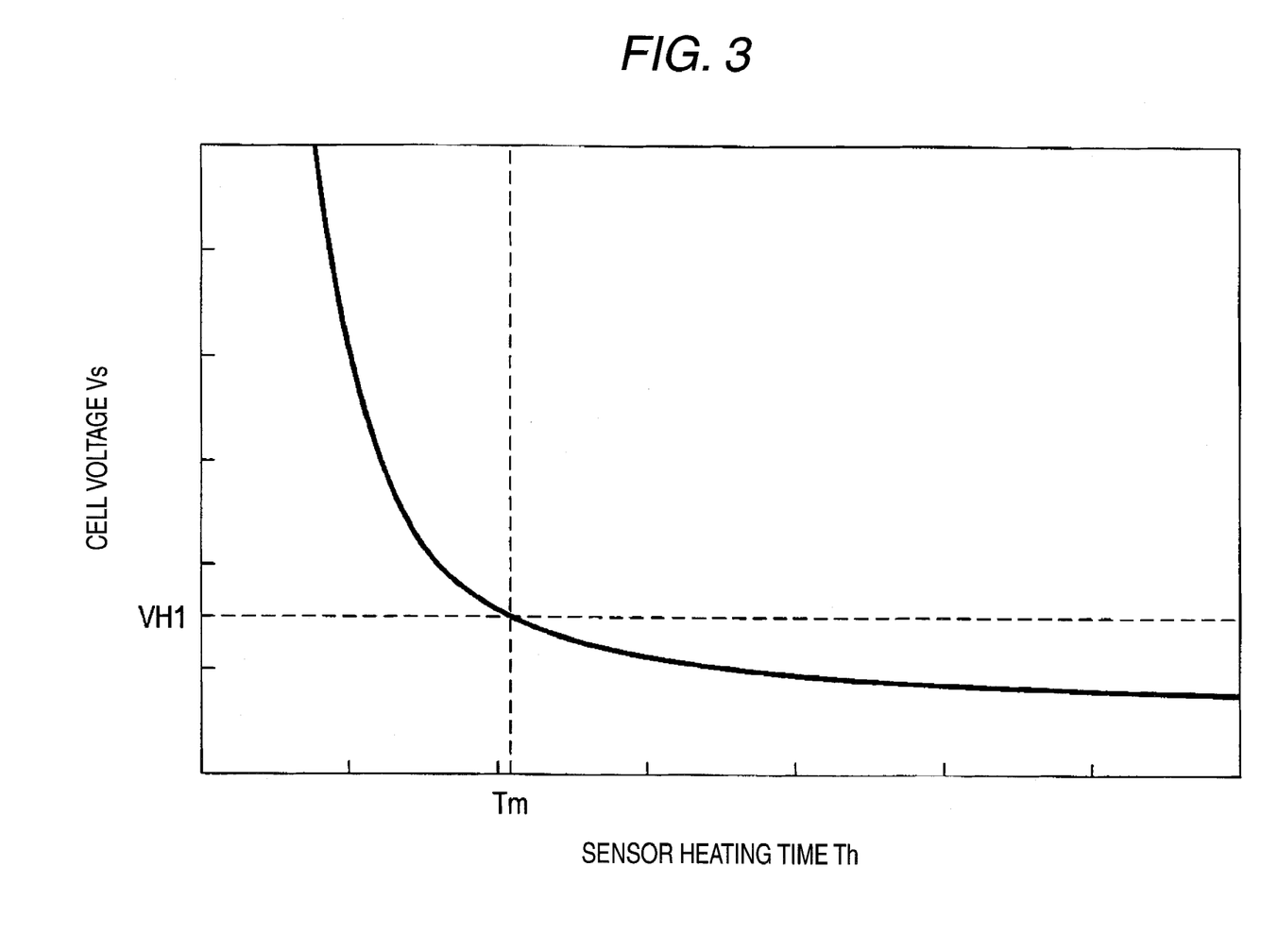
FIG. 3 is a view illustrating a measurement result which is a correlation between a sensor heating time Th and a voltage Vs developed across an oxygen concentration detection cell.

Here, a measurement result, which is obtained by measuring the correlation between the sensor heating time Th and the voltage Vs across both ends of the oxygen concentration detection cell 24 after the start of heating, when the heating of the gas sensor element 10 at the room temperature (here, 25° C.) is started using the actual gas sensor element 10, will be described.

FIG. 3 illustrates a measurement result correlating the sensor heating time Th and the voltage Vs. The voltage Vs of the oxygen concentration detection cell 24 corresponds to the electrical impedance value Rpvs of the oxygen concentration detection cell 24 and indicates a value corresponding to the temperature of the oxygen concentration detection cell 24. More specifically, as the temperature of the oxygen concentration detection cell 24 rises, the electrical impedance value Rpvs of the oxygen concentration detection cell 24 decreases and the voltage Vs of the oxygen concentration detection cell 24 decreases.

As shown in the test result of FIG. 3, the voltage Vs of the oxygen concentration detection cell 24 decreases with time, meaning that the element temperature of the oxygen concentration detection cell 24 is increasing. In addition, a first voltage determination value VH1 shown in FIG. 3 is equivalent to the voltage Vs when the temperature of the gas sensor element 10 is at a blackening avoidance temperature (temperature at which blackening due to application of the reference generation current Icp does not occur in the gas sensor element 10).

That is, the time required until the voltage Vs reaches the first voltage determination value VH1 from the heating start time of the sensor is equivalent to the time (shortest damage avoidance time Tm) required to raise the element temperature of the gas sensor element to the temperature at which damage (for example, blackening) due to application of the reference generation current does not occur.

Accordingly, it is possible to perform such measurement on the gas sensor element, to calculate the shortest damage avoidance time Tm from the measurement result, and to set the damage avoidance threshold value Bt used in step S160 of the after-start state determination processing based on the shortest damage avoidance time Tm.

Next, is a description how the application start time of the reference generation current Icp changes in the internal combustion engine control system 1 of the present embodiment as the element temperature (initial element temperature) of the gas sensor element at the start of sensor heating changes.

Figure 4:
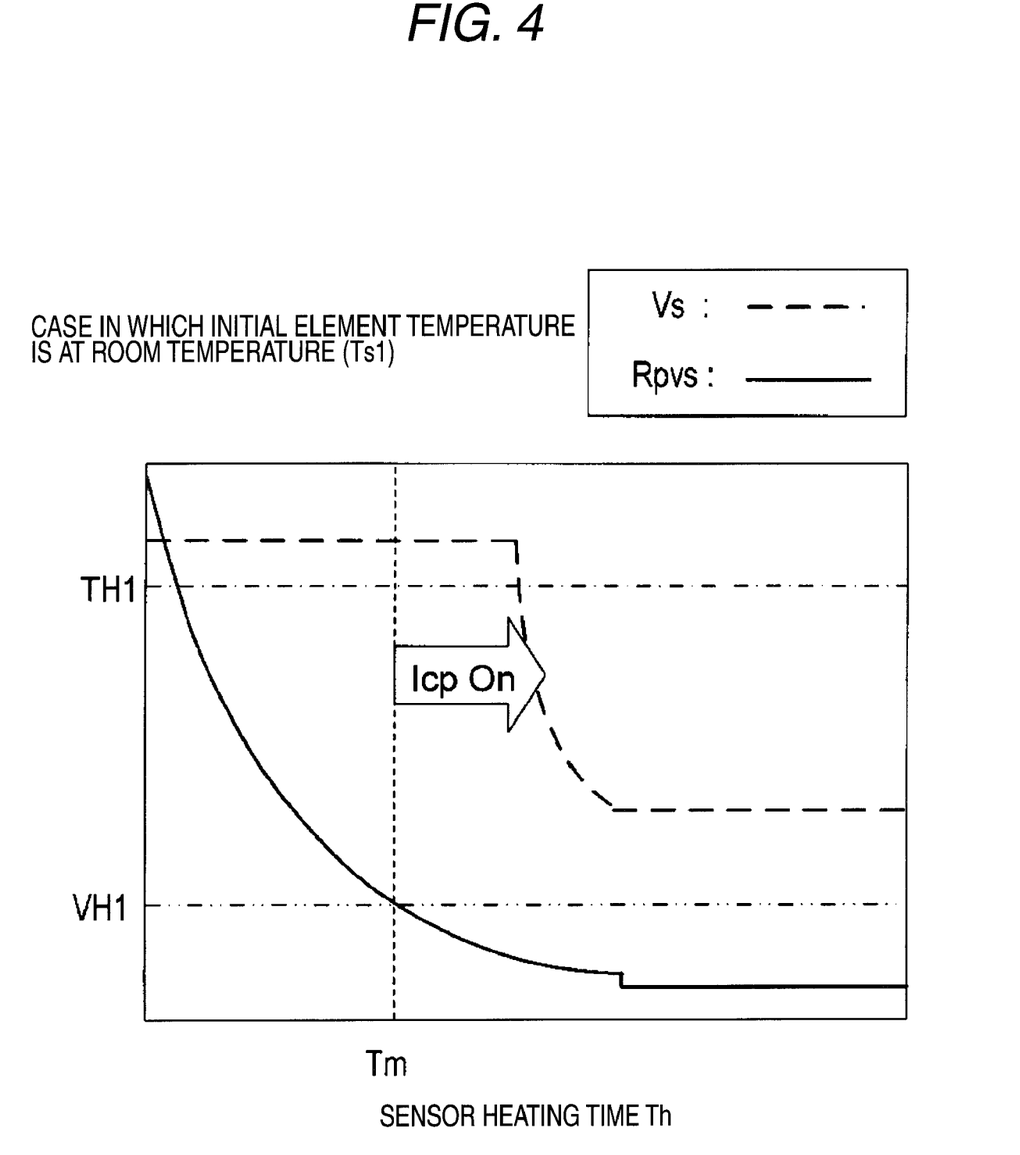
FIG. 4 is an explanatory view illustrating an example of a correlation between the sensor heating time Th and the voltage Vs developed across the oxygen concentration detection cell when the initial element temperature is a room temperature Ts1.

FIG. 4 is an explanatory view illustrating an example of the correlation between the sensor heating time Th and the voltage Vs of the oxygen concentration detection cell 24, and an example of the correlation between the sensor heating time Th and the electrical impedance value Rpvs of the oxygen concentration detection cell 24 when the initial element temperature is at room temperature Ts1. In addition, FIG. 5 is an explanatory view illustrating an example of the correlation between the sensor heating time Th and the voltage Vs of the oxygen concentration detection cell 24, and an example of the correlation between the sensor heating time Th and the electrical impedance value Rpvs of the oxygen concentration detection cell 24 when the initial element temperature is at a temperature Ts2 (relationship of Ts2>Ts1) higher than room temperature Ts1.

First, when the initial element temperature is the room temperature Ts1, the time required until the voltage Vs of the oxygen concentration detection cell 24 reaches the first voltage determination value VH1 is the shortest damage avoidance time Tm, and application of the reference generation current Icp is started at a point of time when the shortest damage avoidance time Tm has elapsed from the start of sensor heating (refer to FIG. 4). At this time, the electrical impedance value Rpvs of the oxygen concentration detection cell 24 indicates a larger value than the first temperature determination value TH1. Accordingly, in the after-start state determination processing, a positive determination is made in step S160 to proceed to step S170 without proceeding to step S170 as a result of a positive determination in step S140, such that application of the reference generation current Icp is started.

Figure 5:
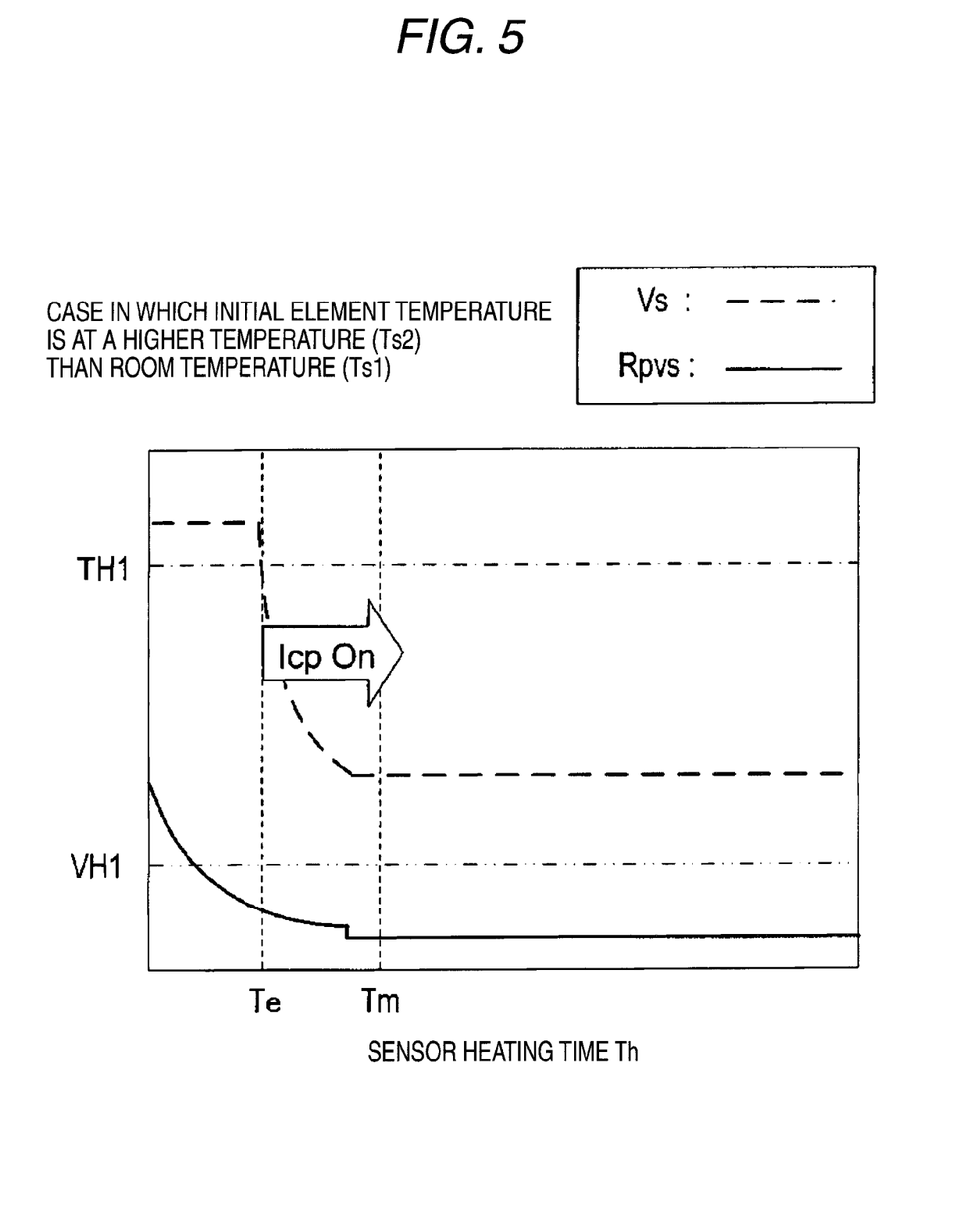
FIG. 5 is an explanatory view illustrating an example of a correlation between the sensor heating time Th and the voltage Vs developed across the oxygen concentration detection cell when the initial element temperature is at a temperature Ts2 higher than the room temperature Ts1.

In addition, when the initial element temperature is a high temperature Ts2, the time required until the voltage Vs of the oxygen concentration detection cell 24 reaches the first voltage determination value VH1 is an early arrival time Te shorter than the shortest damage avoidance time Tm, and application of the reference generation current Icp is started at a point in time when the early arrival time Te has elapsed from the start of sensor heating (refer to FIG. 5). At this time, the electrical impedance value Rpvs of the oxygen concentration detection cell 24 has decreased to a value smaller than that corresponding to the first temperature determination value TH1. Accordingly, in the after-start state determination processing, the positive determination is made in step S140 to proceed to step S170 without proceeding to step S170 as a result of a positive determination in step S160, such that application of the reference generation current Icp is started.

Thus, in the case where the initial element temperature is high, the time until the temperature of the sensor element reaches the current application permission temperature (element temperature set by the first temperature determination value TH1) becomes short. Accordingly, the internal combustion engine control system 1 of the present embodiment starts application of the reference generation current Icp without waiting until the damage avoidance time has elapsed (until the positive determination is made in step S160).

As described above, by using the internal combustion engine control system 1 according to the present embodiment, measurement of the specific gas component concentration (oxygen concentration in the present embodiment) can be executed early under a condition in which the gas sensor element 10 is activated at an early stage.

Modifications:

Next, modifications of the above embodiment will be described. In this modification, the same gas sensor 8 and internal combustion engine control system 1 as in the above embodiment (refer to FIG. 1) are provided. However, the processing flow of the after-start state determination processing in the engine control device 9 (specifically, a microcomputer that constitutes the engine control device 9) is different from that of the above embodiment. Also, processing for causing the reference generation current Icp to flow when the voltage Vs generated across a pair of electrodes of the oxygen concentration detection cell 24 becomes lower than a permission voltage threshold value is added. Therefore, the following explanation focuses on a portion different from the above embodiment, and the same components are denoted by the same symbols or reference numerals and an explanation thereof is omitted or simplified.

Figure 6:
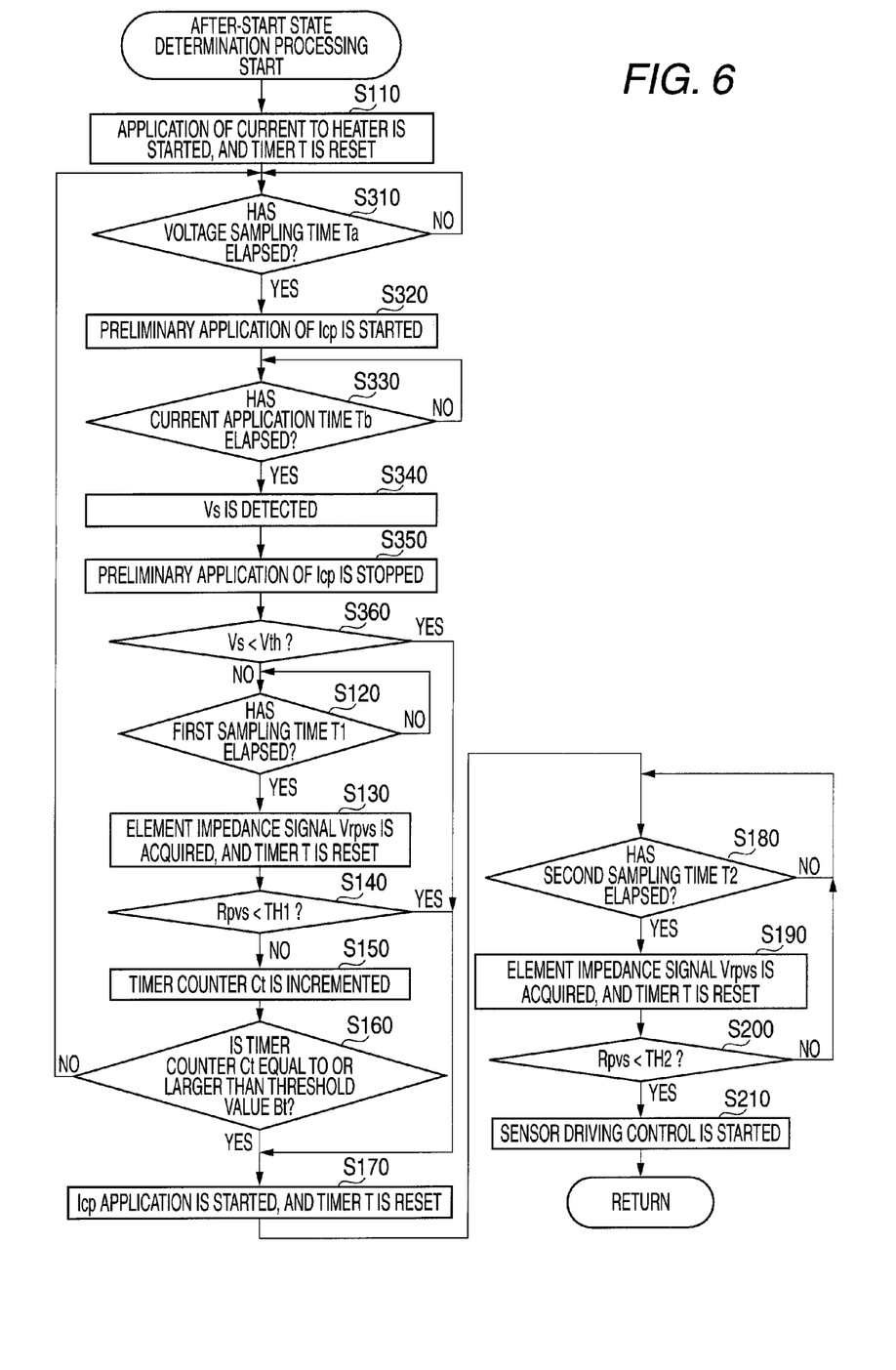
FIG. 6 is a flow chart illustrating processing details of after-start state determination processing in a modification of the embodiment.

Processing details of the after-start state determination processing in the engine control device 9 in this modification will be described according to the flow chart shown in FIG. 6. When the after-start state determination processing is started, processing for current application to the heater 43 is first started in step S110 in the same manner as in the above embodiment. Furthermore, in step S110, after outputting a heater energization command signal, a timer T is reset to start elapsed time measurement processing using the timer T and processing for initializing a timer counter Ct used in internal processing is executed. Then, the process proceeds to step S310.

In step S310, in order to determine the sampling time of the voltage Vs of the oxygen concentration detection cell 24, a determination is made as to whether or not a voltage sampling time Ta has elapsed on the basis of a value of the timer T. Here, if a positive determination is made, the process proceeds to step S320. If a negative determination is made, the same step is repeatedly executed until a voltage sampling time Ta has elapsed. In addition, in step S310, a determination is made as to whether or not the voltage sampling time Ta has elapsed on the basis of the value of the timer T when the measurement has started in step S110 or S130 described below. In addition, the voltage sampling time Ta is set to a time shorter than the first sampling time T1 set in step S130.

When a positive determination is made in step S310 to proceed to step S320, preliminary application of the reference generation current Icp is started to detect a value of the voltage Vs of the oxygen concentration detection cell 24 in step S320. Specifically, the gas sensor driving circuit 2 causes the reference generation current Icp to start flowing through the gas sensor element 10 (specifically, the oxygen concentration detection cell 24) by causing the engine control device 9 to output the Icp current application command signal to the gas sensor driving circuit 2.

Then, the process proceeds to step S330 in which preliminary application of the reference generation current Icp is started, and a determination is then made as to whether or not a current application time Tb has elapsed. Here, if a positive determination is made, the process proceeds to step S340. If a negative determination is made, the same step is repeatedly executed until the current application time Tb has elapsed. In addition, also in step S330, a determination is made as to whether or not the current application time Tb has elapsed on the basis of the value of the timer T when the measurement has started in step S110 or S130 described below. In addition, the current application time Tb is set beforehand to a time which is shorter than the shortest damage avoidance time described in the above embodiment and for which damage caused by current application does not occur in the oxygen concentration detection cell 24. In addition, the current application time Tb corresponds to a "voltage detection time" of the present invention.

When a positive determination is made in step S330 to proceed to step S340, a value of the both-ends voltage Vs of the oxygen concentration detection cell 24 (i.e., the voltage developed across the oxygen concentration cell 24) is detected in step S340. Then, the process proceeds to step S350 to stop preliminary application of the reference generation current Icp.

In the following step S360, a determination is made as to whether or not the value of the voltage Vs is smaller than a voltage permission threshold value Vth. If a positive determination is made, the process proceeds to step S170. If a negative determination is made, the process proceeds to step S120. That is, in step S360, a determination is made as to whether or not the element temperature of the gas sensor element 10 exceeds the blackening avoidance temperature based on the value of the voltage Vs.

In addition, the details of processing following step S170 after the positive determination is made in step S360 and processing following step S120 after the negative determination is made in step S360 are the same as those in the embodiment described above. However, when a negative determination is made in step S160, it is set to return to the processing of step S310.

Also by executing the after-start state determination processing in such modification, application of the reference generation current Icp to the gas sensor driving circuit 2 can be prevented in a situation where the temperature of the gas sensor element 10 is low, such as a situation immediately after the start of sensor heating by the heater 43 and the heater control circuit 60. As a result, it is possible to prevent the gas sensor element 10 from becoming damaged. In addition, application of the reference generation current Icp can be started by the gas sensor driving circuit 2 without waiting for the damage avoidance time to elapse in the case where the value of the voltage Vs of the oxygen concentration detection cell 24 becomes lower than the current application permission threshold value, or where the element temperature of the gas sensor element 10 reaches the current application permission temperature before the damage avoidance time has elapsed.

In addition, in this modification, the engine control device 9 and the gas sensor driving circuit 2 that executes steps S320, S330 and S350 correspond to a current application unit, the engine control device 9 that executes step S340 corresponds to a voltage detecting unit, and the engine control device 9 that executes step S360 corresponds to a permission voltage determining unit.

Having described the embodiment of the present invention, the present invention is not limited to the above-described embodiment but various modifications may be made.

For example, the above embodiment (hereinafter, referred to as a first embodiment) is configured such that a determination is made as to whether or not the damage avoidance time has elapsed (S160), or whether or not the element temperature is higher than the current application permission temperature (S140). Then, application of the reference generation current Icp is permitted if one of the two determination conditions is satisfied. However, under the condition in which the initial element temperature is fixed, a configuration may be adopted where the only determination that is made is whether or not the damage avoidance time has elapsed, and then application of the reference generation current Icp is permitted if the determination condition is satisfied.

In addition, although the sensor element which detects oxygen has been described in the first embodiment, the present invention may also be applied to a sensor control device which controls a sensor element that detects specific gas (for example, NOx) other than oxygen. In addition, the gas sensor element is not limited to a two cell type element having an oxygen concentration detection cell and an oxygen pump cell, but may be a gas sensor (a one cell-type gas sensor) having one cell or a gas sensor having three or more cells.

It should further be apparent to those skilled in the art that various changes in form and detail of the invention as shown and described above may be made. It is intended that such changes be included within the spirit and scope of the claims appended hereto.

This application claims the benefit of Japanese Patent Application JP 2007-122543, filed May 7, 2007, the entire content of which is hereby incorporated by reference, the same as if set forth at length.

What is claimed is:

1. A sensor control device that controls application of a current to a gas sensor element that measures a specific gas component concentration in a gas to be measured, the sensor control device comprising:
at least one cell comprising a solid electrolyte body and a pair of electrodes;
a sensor heating unit that heats the gas sensor element;
an oxygen reference pole generating unit that causes a reference generation current to flow through the at least one cell so as to establish a first one of the pair of electrodes of the cell as an oxygen reference pole;
a damage avoidance time elapse determining unit that determines, in response to the sensor heating unit starting to heat the gas sensor element, whether a preset damage avoidance time has elapsed from a time at which the starting occurs;
a reference generation current application permitting unit that controls the oxygen reference pole generating unit to not cause the reference generation current to flow through the at least one cell in response to the damage avoidance time elapse determining unit determining that the damage avoidance time has not elapsed, and controls the oxygen reference pole generating unit to cause the reference generation current to flow through the at least one cell in response to the damage avoidance time elapse determining unit determining that the damage avoidance time has elapsed;
an element temperature detecting unit that detects a temperature of the gas sensor element;
a permission temperature determining unit that compares a current application permission temperature, which is set based on an activation temperature of the gas sensor element, with the element temperature detected by the element temperature detecting unit, and determines whether the element temperature is higher than the current application permission temperature;
a current application unit that causes a current to flow through the at least one cell, through which the reference generation current is passed, during a preset voltage detection time which is shorter than the damage avoidance time and for which damage caused by current application does not occur;
a voltage detecting unit that detects a value of a voltage developed across the pair of electrodes of the at least one cell when a current is caused to flow through the at least one cell by the current application unit; and
a permission voltage determining unit that compares a voltage value detected by the voltage detecting unit with a current application permission threshold value, and determines whether or not the voltage value is higher than the current application permission threshold value,
wherein the reference generation current application permitting unit controls the oxygen reference pole generating unit to cause the reference generation current to flow through the at least one cell in response to the damage avoidance time elapse determining unit determining that the damage avoidance time has elapsed, when the permission temperature determining unit determines that the element temperature is higher than the current application permission temperature, or when the permission voltage determining unit determines that the voltage value is lower than the current application permission threshold value,
wherein the preset damage avoidance time is an amount of time the heating unit heats the gas sensor element to a temperature at which blackening of the gas sensor element is prevented when the reference generation current is applied to the gas sensor element.

2. The sensor control device according to claim 1, wherein the voltage detecting unit detects a value of the voltage developed across the pair of electrodes of the at least one cell when the reference generation current application permitting unit controls the oxygen reference pole generating unit to cause a current to flow through the at least one cell by using the oxygen reference pole generating unit as the current application unit.

3. The sensor control device according to claim 2, wherein the gas sensor element comprises:
a measurement chamber communicating with the gas to be measured through a diffusion resistance portion;
an oxygen concentration detection cell in which one of a pair of electrodes is blocked so as not to be exposed to the gas to be measured and the other electrode is disposed facing the measurement chamber and which generates a voltage between the pair of electrodes corresponding to an oxygen concentration of the measurement chamber; and an oxygen pump cell in which one of a pair of electrodes is disposed facing the measurement chamber and the other electrode is disposed facing the gas to be measured and which pumps oxygen into or out of the measurement chamber according to a current flowing between the pair of electrodes, wherein the oxygen reference pole generating unit is connected to the oxygen concentration detection cell such that the one of a pair of electrodes of the oxygen concentration detection cell becomes an oxygen reference pole.

4. The sensor control device according to claim 1, wherein the gas sensor element comprises:

a measurement chamber communicating with the gas to be measured through a diffusion resistance portion;

an oxygen concentration detection cell in which one of a pair of electrodes is blocked so as not to be exposed to the gas to be measured and the other electrode is disposed facing the measurement chamber and which generates a voltage between the pair of electrodes corresponding to an oxygen concentration of the measurement chamber; and an oxygen pump cell in which one of a pair of electrodes is disposed facing the measurement chamber and the other electrode is disposed facing the gas to be measured and which pumps oxygen into or out of the measurement chamber according to a current flowing between the pair of electrodes, wherein the oxygen reference pole generating unit is connected to the oxygen concentration detection cell such that the one of a pair of electrodes of the oxygen concentration detection cell becomes an oxygen reference pole.

5. The sensor control device according to claim 1, wherein the gas sensor element comprises:

a measurement chamber communicating with the gas to be measured through a diffusion resistance portion;

an oxygen concentration detection cell in which one of a pair of electrodes is blocked so as not to be exposed to the gas to be measured and the other electrode is disposed facing the measurement chamber and which generates a voltage between the pair of electrodes corresponding to an oxygen concentration of the measurement chamber; and an oxygen pump cell in which one of a pair of electrodes is disposed facing the measurement chamber and the other electrode is disposed facing the gas to be measured and which pumps oxygen into or out of the measurement chamber according to a current flowing between the pair of electrodes, wherein the oxygen reference pole generating unit is connected to the oxygen concentration detection cell such that the one of a pair of electrodes of the oxygen concentration detection cell becomes an oxygen reference pole.

* * * * *